United States Patent [19]

Saville

[11] Plant 5,094

[45] Aug. 30, 1983

[54] ROSE PLANT

[75] Inventor: F. Harmon Saville, Rowley, Mass.

[73] Assignee: Nor'East Miniature Roses, Inc., Rowley, Mass.

[21] Appl. No.: 382,588

[22] Filed: May 27, 1982

[51] Int. Cl.[3] ..... A01H 5/00

[52] U.S. Cl. ..... Plt./7

[58] Field of Search ..... Plt./7

*Primary Examiner*—James R. Feyrer

*Attorney, Agent, or Firm*—Vincent G. Gioia

[57] ABSTRACT

A new "hand painted" miniature rose variety of red and yellow coloring changing to pink and white.

1 Drawing Figure

The present invention relates to a new and distinct variety of rose plant of the hybrid tea rose class, which was originated by my crossing as seed parent my seedling of (Tamango × Yellow Jewel) and the rose known as "Sheri Anne" as pollen parent (U.S. Plant Pat. No. 3,826). The denomination of the new variety is "Savapaint".

Among the novel characteristics possessed by this new variety which distinguish it from its parents and all other varieties of which I am aware are multi-colored "hand painted" flowers varying in coloring from bright red and deep yellow as flowers open to Neyron rose and white as blooms age. Asexual reproduction by budding of the new variety as performed in Essex County, Mass., shows that the foregoing and other distinguishing characteristics come true to form and are establishd and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Color Chart (RHSCC). The terminology used in color description herein refers to plate numbers in the aforementioned color chart, e.g., "11B" is plate 11B of The Royal Horticultural Society Color Chart.

Parentage: Seedling.

*Seed parent.*—My unpatented, unreleased seedling of (Tamango × Yellow Jewel).

*Pollen parent.*—"Sheri Anne".

Class: Miniature.

The following observations are made of specimens grown under glass in Essex County, Mass. during the month of April.

FLOWER

Blooming habit: Recurrent.

A. Bud:

(1) *Size.*—Medium.

(2) *Form.*—Ovate to short pointed.

(3) *Color.*—After sepals fall, 11B.

(4) *Sepals.*—Smooth, slightly longer than bud.

(5) *Peduncle.*—Length — about $\frac{5}{8}$ to $\frac{3}{4}$ inches. Aspect — straight. Strength — erect. Color — near 144C.

b. Bloom:

(1) *Size.*—Average size when fully expanded — about $1\frac{1}{4}$ inches.

(2) *Borne.*—Singly and small sprays.

(3) *Form.*—Cupped at first becoming flat.

(4) *Petalage.*—Number of petals under normal conditions — about 15.

(5) *Color.*—A miniature rose of multi-coloring having a "hand painted" effect. Relatively short Naples yellow buds, the color of the petal undersurface, open with deep color tones. The petal top surface is "piebald" with a series of colors, the deepest color tone being current red 46A, and chrome yellow 15C. Some petals show stippling with most petals showing solid red color segments. In newly opened blooms the bright red coloring seems to surround a deep yellow center formed by the yellow petal color at the lower $\frac{1}{3}$ of each petal enhanced by stamens of similar deep yellow coloring. As flowers age, the red coloring wherever appearing, changes to 53B (at its darkest intermediate coloring) and continues to lighten to Neyron rose 55C and 55D, becoming more stippled as it ages. The yellow lightens with fewer intermediate tones becoming, ultimately, almost clear white. The stamens, clearly visible in open blooms, darken to brown.

C. Petals:

(1) *Texture.*—Thick.

(2) *Appearance.*—Inside velvety, outside satiny.

(3) *Form.*—Fan shaped, reflex as flower opens.

(4) *Arrangement.*—Imbricated, regularly arranged shingle-like.

(5) *Petaloids in center.*—Few.

(6) *Persistence.*—Drop off cleanly after 2–12 days.

(7) *Fragrance.*—Slight.

(8) *Lasting quality.*—Very long lasting on plant and as cut flower.

REPRODUCTIVE ORGANS

A. Stamens, filaments and anthers:

(1) *Arrangement.*—Stamens regularly arranged around styles.

(2) *Color.*—Near 17C.

B. Pollen:

*Color.*—Near 17B.

C. Styles: Bunched.

D. Stigmas:

*Color.*—Near 157C.

E. Hips: None observed.

PLANT

A. Form: Upright, compact.

B. Growth: Vigorous.

*Height attained.*—About 12 to 14 inches.

C. Foliage: Compound 5 to 7 leaflets (1) *Size.*—Medium.

(2) *Quantity.*—Abundant.

(3) *Color.*—New foliage: Upper side — near to 137C; Under side — near to 148C. Old foliage: Upper side — near 137B; Under side — near 148C.

(4) *Shape.*—Oval, cuspidate.

(5) *Texture.*—Upper side is semi-glossy and under side is matte.

(6) *Edge.*—Serrated.

(7) *Serration.*—More conspicuous at outer ½ of leaflet.

(8) *Leaf stem.*—Color — near to 181B. Under side — near 146C.

(9) *Stipules.*—Medium smooth.

(10) *Resistance to disease.*—Blackspot — average. Mildew — average. Rust — average.

D. Wood:

(1) *New wood.*—Color — near 146B. Bark — smooth.

(2) *Old wood.*—Color — near 152D. Bark — smooth.

E. Thorns:

(1) Thorns.—Quantity (main stalk) — none. On laterals from talk — none.

(2) *Prickles.*—None.

F. Winter hardiness: Needs protection in severe climate.

I claim:

1. A new and distinct variety of rose plant of the miniature rose class, substantially as shown and described, characterized particularly by "hand painted" flowers starting with current red and chrome yellow coloring changing to Neyron rose and white as flowers age.

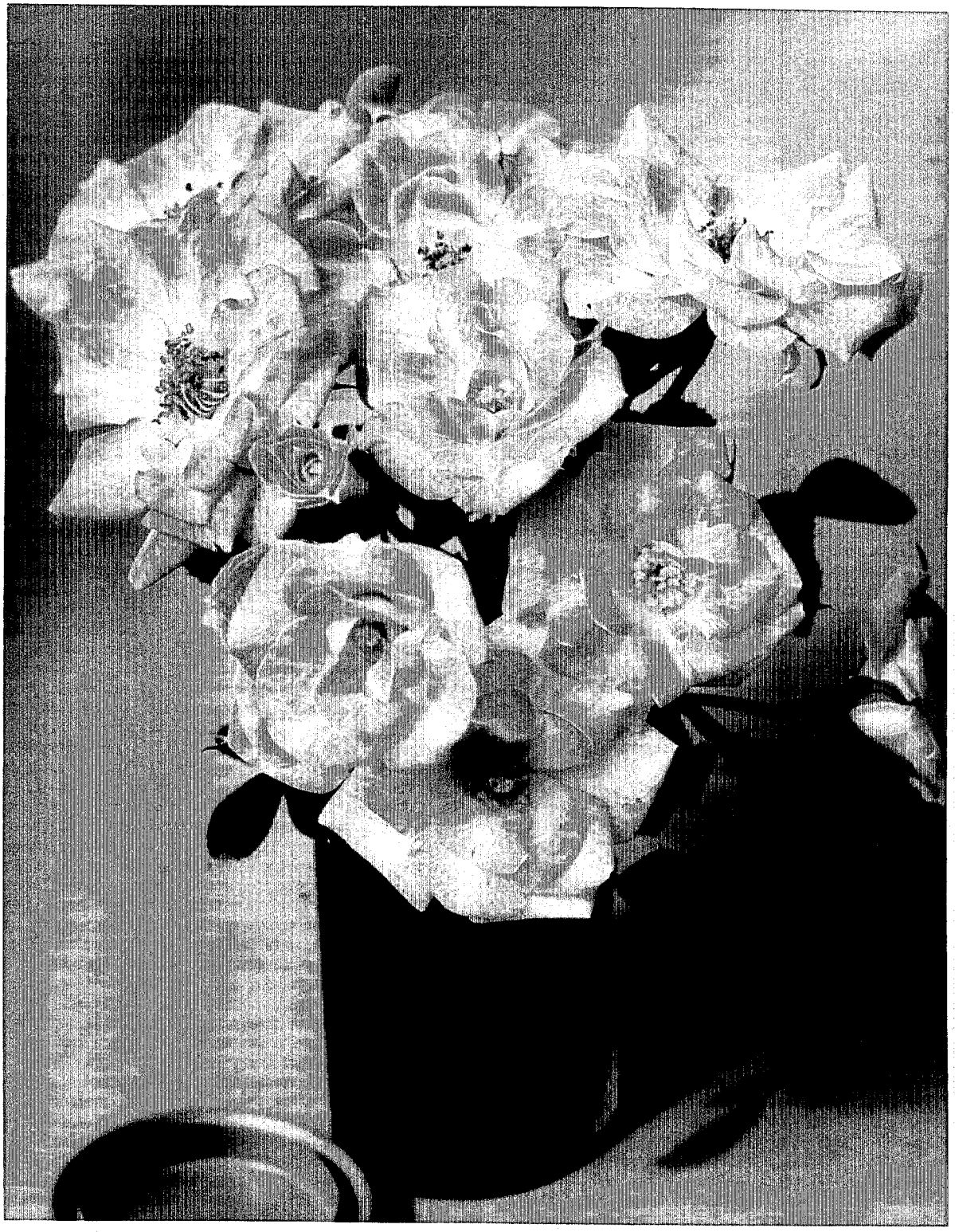

* * * * *